United States Patent [19]

Hanreich

[11] Patent Number: 4,959,501
[45] Date of Patent: * Sep. 25, 1990

[54] PROCESS FOR THE PREPARATION OF 2-(2-CHLOROETHOXY)-BENZENESULFONAMIDE

[75] Inventor: Reinhard G. Hanreich, Basle, Switzerland

[73] Assignee: Ciba-Geigy Corporation, Ardsley, N.Y.

[ * ] Notice: The portion of the term of this patent subsequent to Feb. 21, 2006 has been disclaimed.

[21] Appl. No.: 197,480

[22] Filed: May 23, 1988

Related U.S. Application Data

[63] Continuation-in-part of Ser. No. 93,436, Sep. 4, 1987, Pat. No. 4,806,528.

[51] Int. Cl.$^5$ ............................................. C07C 143/78
[52] U.S. Cl. .................................................. 564/89
[58] Field of Search ................... 564/89; 568/649; 260/512 R

[56] References Cited

U.S. PATENT DOCUMENTS

| | | |
|---|---|---|
| 2,416,263 | 2/1947 | MacMullen . |
| 4,476,321 | 10/1984 | Meyer et al. . |
| 4,514,212 | 4/1985 | Meyer et al. . |
| 4,556,733 | 12/1985 | Sullivan et al. . |
| 4,709,092 | 11/1987 | Jaeggi . |
| 4,806,528 | 2/1989 | Hanreich .......................... 564/89 |

*Primary Examiner*—Alan Siegel
*Attorney, Agent, or Firm*—Kevin T. Mansfield; Edward McC. Roberts

[57] ABSTRACT

In accordance with a novel process, 2-(2-chloroethoxy)-benzenesulfonamide of formula I

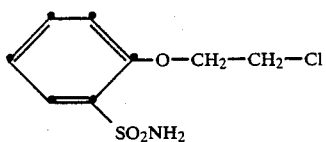
(I)

is prepared by etherification of 4-chlorophenol of formula II

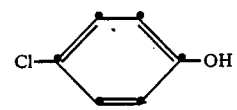
(II)

with ethylene carbonate and chlorination of the resulting 4-(2-hydroxyethoxy)-chlorobenzene of formula III

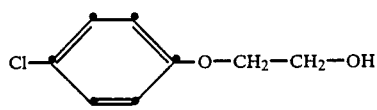
(III)

with phosgene or thionyl chloride to give 4-(2-chloroethoxy)-chlorobenzene of formula IV

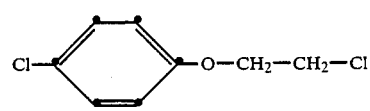
(IV)

which is converted with chlorosulfonic acid ClSO$_3$H and sodium hydroxide to the sulfonic acid sodium salt of formula V

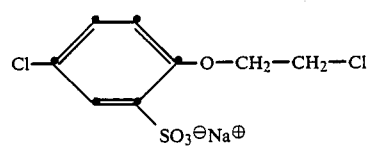
(V)

which is hydrogenated to the compound of formula VI

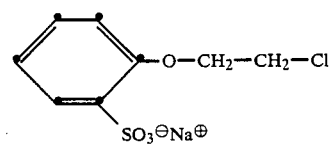
(VI)

which is subsequently reacted with phosgene to the sulfonic acid chloride of formula VII

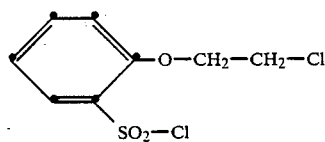
(VII)

which is reacted with amonia to the sulfonamide of formula I.

13 Claims, No Drawings

PROCESS FOR THE PREPARATION OF 2-(2-CHLOROETHOXY)-BENZENESULFONAMIDE

CROSS REFERENCE TO RELATED APPLICATION

This is a continuation-in-part of application Ser. No. 093,436, filed Sept. 4, 1987, now U.S. Pat. No. 4,806,528.

The present invention relates to a novel process for the preparation of 2-(2-chloroethoxy)-benzenesulfonamide.

The 2-(2-chlorethoxy)-benzenesulfonamide which can be prepared by the novel process is a valuable intermediate for the synthesis of herbicidal 4-(2-chloroethoxy)-benzenesulfonylureas. This class of highly effective herbicides has recently been described in a number of patent applications and publications. The 4-(2-chloroethoxy)-benzenesulfonamide which can be prepared by the process of this invention, the preparation thereof and the use thereof in the synthesis of the herbicidal final products from the class of sulfonylureas are described in the European patent No. 44 808.

The processes hitherto described for the preparation of alkoxybenzenesulfonamides are less suitable for large-scale industrial application since either unstable diazonium salts are obtained as intermediates and the exchange reaction of the Sandmeyer-type with Cu(I) compounds has only an insufficient degree of selectivity or product mixtures are formed which require complicated separation methods.

There is therefore a need for an inexpensive process for the preparation of 2-(2-chloroethoxy)-benzenesulfonamide, which process can be carried out on a large industrial scale.

Surprisingly, the novel process of this invention substantially meets these requirements.

In accordance with the present invention, it is proposed to prepare the 2-(2-chloroethoxy)-benzenesulfonamide of formula I

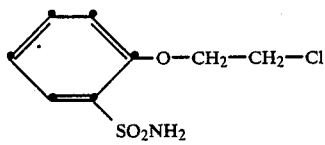

by etherification of 4-chlorophenol of formula II

with ethylene carbonate and chlorination of the resulting 4-(4-hydroxyethoxy)-chlorobenzene of formula III

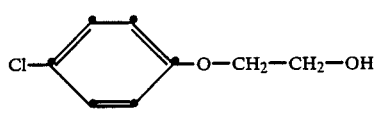

with phosgene or thionyl chloride to give 4-(2-chloroethoxy)-chlorobenzene of formula IV

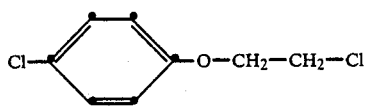

which is converted with chlorosulfonic acid $ClSO_3H$ and sodium hydroxide to the sulfonic acid sodium salt of formula V

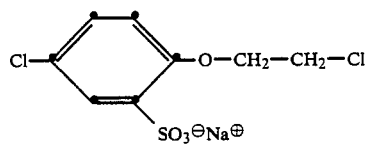

which is hydrogenated to the compound of formula VI

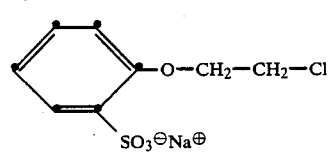

which is subsequently reacted with phosgene to the sulfonic acid chloride of formula VII

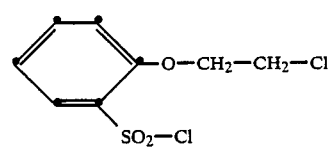

which is reacted with ammonia to the sulfonamide of formula I.

The 2-(2-chloroethoxy)-benzenesulfonamide formed by the novel process is of high purity. It can be converted directly into an agriculturally useful active ingredient of the class of sulfonylureas in a manner known per se by reaction with a suitable pyrimidinylcarbamate or triazinylcarbamate or with a corresponding isocyanate. As an alternative to this process, the 2-(2-chloroethoxy)-benzenesulfonamide of formula I is first converted into the corresponding isocyanate or carbamate which are then reacted with suitable pyrimidinylamines or triazinylamines to give effective sulfonylureas.

The starting material of formula II is known and commercially available.

Commercially available ethylene carbonate (1,3-dioxolan-2-one) and phosgene or thionyl chloride are used for carrying out the first two reaction steps (II→III→IV). These two reactions can be carried out in a single vessel without isolating the intermediate of formula III. It is noteworthy that the neat starting materials II, ethylene carbonate and phosgene or thionyl chloride can be used without a solvent in the first two steps. The reaction temperature for the first step (II→III) is in the range of +130° C. to +150° C. Preferably this step is performed in the presence of a catalytic amount of a tertiary amine such as tributylamine or 1,8-diazabicyclo[5.4.0]undec-7-ene. The reaction temperature for the second step (III→IV) is in the range of +70° C. to +90° C. Preferably this step is carried out in the presence of a catalytic amount of dimethylformamide or dimethylacetamide. Dimethylformamide is preferred.

The crude reaction mixture after the reaction sequence (II→III→IV) in a single-vessel-procedure is worked up with addition of diluted sodium hydroxide solution and subsequent destillation of the compound of formula IV. This procedure yields the intermediate of formula IV in high purity.

Commerically available chlorosulfonic acid is used for carrying out the third step (IV→V) of the process of this invention. To effect reaction an equimolar amount of chlorosulfonic acid is used per mole of the compound of formula IV.

In accordance with this process variant, the reaction temperature is in the range from −20° C. to +60° C., preferably from −10° C. to +5° C. Working up by neutralisation of the reaction mixture with aqueous sodium hydroxide, at a temperature in the range from +50° C. to +90° C., preferably from +60° C. to +80° C., yields the corresponding sulfonic acid sodium salt of formula V. In a preferred work up procedure, the reaction mixture is diluted with water, extracted with toluene or xylene at a temperature between 0° C. and +50° C., preferably between +20° C. and +40° C., the aqueous solution is neutralized with sodium hydroxide at a temperature between +50° C. and +70° C.

This reaction is advantageously carried out in an inert solvent such as an alkane or chloroalkane such as pentane, hexane, heptane, octane, decane, dodecane, and also cyclopentane, cyclohexane or decaline, as well as methylene chloride, chloroform, carbon tetrachloride, dichloroethane, trichlorethane or tetrachloroethane. Hexane and n-decane are preferred.

The dechlorination of the compound of formula V to give the compound of formula VI by catalytic hydrogenation with hydrogen is generally carried out under mild conditions, in the temperature range from +20° C. to +70° C., preferably from +40° C. to +60° C., in the pressure range from 1 to 5 bar, preferably from 1 to 4 bar, in an inert solvent and in the presence of an acid acceptor. In general, the catalysts employed are precious metal catalysts such as platinum in the form of platinum oxide or palladium, platinum black or platinum on barium sulfate, palladium black or palladium on carbon. The catalyst which can be most widely used is palladium on carbon in commercially available form as 5% palladium on carbon. The acid acceptor normally employed is sodium hydroxide. This base is preferably added to the reaction mixture continuously in order to maintain a constant pH-value, in the present case between pH 9.5 and 11.5. In the preferred embodiment, the compound of formula V is hydrogenated with hydrogen, under normal pressure, in the temperature range from +40° C. to +60° C. and in the presence of a 5% palladium on carbon catalyst in a mixture of base and water.

After the completion of the hydrogenating reaction the catalyst is removed from the mixture by filtration or sedimentation. In the preferred over-all reaction, the filtrate is dried by addition of chlorobenzene and subsequent destilling off the azeotropic destillate. In said preferred procedure, the remaining slurry of 2-(2-chloroethoxy)-benzenesulfonic acid sodium salt is directly introduced into the next reaction step (VI→VII).

The compound of formula VI is converted into the sulfonyl chloride of formula VII by reaction with gaseous phosgene. For econonomical and ecological reasons the phosgene is preferably generated in a continuous phosgene generator without intermediate storage of said phosgene. It is advantageous to use a catalyst such as dimethylformamide or dimethylacetamide. The reaction conditions for the genesis of the sulfonyl chloride from the sodium salt (VI→VII) correspond to the usual conditions for this type of reaction. The exclusion of moisture and inertness of the solvent are essential features. Such conditions are indicated above. Preferred reaction temperatures are in the range from +60° C. to +120° C., with about +95° C. being especially suitable. In the preferred over-all-reaction the excess of phosgene is removed from the solution by washing it with water. The organic layer is filtered and directly introduced into the following reaction step (VII→I).

The conversion of the sulfonic acid chloride of formula VII into the corresponding sulfonamide of formula I is effected under the conditions usual for this per-se-known reaction step, for example by adding an aqueous solution of ammonia to the compound of formula VII, under normal pressure and at a temperature in the range from 0° C. to +100° C., preferably from +50° C. to +70° C. The reaction is preferably carried out with an aqueous solution of ammonia which is added to the sulfonic acid chloridesolution as obtained from the chlorination step (VI→VII).

After completion of the amidation reaction (VII→I) the aqueous phase containing water and excess ammonia is destilled off azeotropically at +70° C. at 80 mbar. The resulting suspsension is filtered at +100° C. over charcoal. After cooling the filtrate to +10° C. the sulfonamide of formula I crystallizes in 70% yield [calculated on 4-chlor-2-(chloroethoxy)-benzene] and 98 to 99% purity.

In a preferred mode of performing the process of the invention, the compound of formula IV is reacted to the compound of formula I, without isolating the intermediates of formulae V, VI and VII.

In said preferred process the compound of formula IV is treated with 1 equivalent of chlorosulfonic acid in hexane or n-decane at a temperature between −10° C. and +5° C.; quenched with water, extracted with xyleneneutralized with aqueous sodium hydroxide at a temperature between +50° C. and +70° C.; dechlorinated with hydrogen in the presence of an acid acceptor, in the pressure range from 1 to 5 bar at a temperature between +20° C. and +70° C. and in the presence of a 5% palladium on carbon catalyst; converted to the sulfonic acid chloride by treatment of the mixture with phosgene at a temperature between +60° C. and +120° C.; and subsequently reacted to the final product by treatment of the reaction mixture with an aqueous solution of ammonia.

In an even more preferred variant, the performance of the process of the invention comprises isolating the compound of formula IV as only intermediate, i.e. the reaction of the compound of formula II to the compound of formula I is carried out without isolating the intermediates of formulae III, V, VI and VII.

In a much preferred process variant the compound of formula II is reacted with ethylene carbonate in the presence of a catalytic amount of tributylamine at a temperature between +130° C. and +150° C.; the resulting reaction mixture is treated with phosgene or thionyl chloride in the presence of a catalytic amount of dimethylformamide at a temperature between +70° C. and +90° C. yielding the compound of formula IV, which after purification is treated with 1 equivalent of chlorosulfonic acid in hexane or n-decane at a temperature between −10° C. and +5° C.; quenched with water, extracted with xylene, neutralized with aqueous sodium hydroxide at a temperature between +50° C. and +70° C.; dechlorinated with hydrogen in the presence of an acid acceptor, in the pressure range from 1 to 5 bar at a temperature between +20° C. and +70° C. and in the presence of a 5% palladium on carbon catalyst; converted to the sulfonic acid chloride by treatment of the mixture with phosgene at a temperature between +60° C. and +120° C.; and subsequently reacted to the final product by treatment of the reaction mixture with an aqueous solution of ammonia.

The most preferred procedure of the process of this invention is wherein the compound of formula II is reacted with ethylene carbonate in the presence of a catalytic amount of tributylamine at a temperature between +130° C. and +150° C.; the resulting reaction mixture is treated with thionyl chloride in the presence of a catalytic amount of dimethylformamide at a temperature between +70° C. and +90° C. yielding the compound of formula IV, which after purification is treated with 1 equivalent of chlorosulfonic acid in n-decane at a temperature between −10° C. and +5° C.; quenched with water, extracted with xylene, neutralized with aqueous sodium hydroxide at a temperature between +50° C. and +70° C.; dechlorinated with hydrogen in the presence of sodium hydroxide, in the pressure range from 1 to 4 bar at a temperature between +40° C. and +60° C. and in the presence of a 5% palladium on carbon catalyst; converted to the sulfonic acid chloride by treatment of the mixture with phosgene at a temperature of +95° C.; and subsequently reacted to the final product by treatment of the reaction mixture with an aqueous solution of ammonia at a temperature of +60° C.

PREPARATORY EXAMPLES

EXAMPLE P1

4-Chloro-(2-chloroethoxy)-benzene 26.4 g of 4-chlorophenol and 18.7 g of ethylene carbonate are heated slowly to +150° C. after addition of 1 g of tributylamine. The reaction mixture is kept at +150° C. during approximately 3 hours until the evolution of carbon dioxide gas ceased. The reaction mixture then is cooled to +85° C. and 1 g of dimethylformamide is added. Subsequently 24 g of phosgene are bubbled through the mixture. The reaction temperature is kept at +85° C. for eight hours and then lowered to +60° C. 100 ml of water are added to destroy an excess of phosgene and subsequently the mixture is neutralized with 10.5 g of a 25% aqueous solution of sodium hydroxide. The organic layer is separated and distilled at 150°–152° C./40 mb to give 36.0 g (93% yield) of 4-chloro-(2-chloroethoxy)-benzene.

EXAMPLE P2

4-Chloro-(2-chloroethoxy)-benzene

After addition of 112.4 g of tributylamine to a mixture of 778.8 g of 4-chlorophenol and 560 g of ethylene carbonate, the resulting mixture is slowly heated to +150° C. The reaction mixture is kept at +150° C. during approximately 3 hours until the evolution of carbon dioxide gas ceased. Most of the tributylamine in the crude mixture is distilled off at +95° C. to +105° C./35 mbar. Subsequently the remaining 4-(2-hydroxyethoxy)-chlorobenzene is treated dropwise with a total of 785.4 g of thionyl chloride at +85° C. to +90° C. in the presence of 13.2 g of dimethylformamide. Vigorous evolution of hydrogen chloride and sulfur dioxide gas is observed. After 4 hours the thionyl chloride addition is completed and the reaction mixture is quenched with 500 ml water at +30° C. to +50° C. The resulting two phase system is neutralized with 384 g of 30% aqueous sodium hydroxide solution at +50° C. to +60° C. The organic layer is separated and distilled at +87° C. to +95° C./5 mbar to give 1044 g (90% yield) of 4-chloro-(2-chloroethoxy)-benzene.

EXAMPLE P3

2-(2-Chloroethoxy)-benzenesulfonamide (a) 124.7 g of chlorosulfonic acid are added over 2 hours to a solution of 203 g of 4-chloro-(2-chloroethoxy)-benzene in 230 ml of n-decane at a temperature in the range from +35° C. to +40° C. Hydrogen chloride gas is evolved and a coarse precipitate is formed. The final suspension is kept for another two hours at +35° C. to +40° C. After that the reaction mixture is quenched with 400 ml of water and then neutralized with 158 g of a 30% aqueous solution of sodium hydroxide at a temperature in the range from +60° C. to +65° C. The aqueous layer (885 g) is separated hot and directly used for the hydrogenation.

(b) In an agitator flask 15 g of palladium 5% on carbon catalyst is added to the above obtained sodium salt solution (885 g) at +40° C. to +45° C. This mixture is hydrogenated with hydrogen under normal pressure in a temperature range form +40° C. to +60° C. The pH of the reaction mixture is kept between 9.5–11.5 by continuous addition of 126.5 g of a 30% aqueous sodium hydroxide solution. When no hydrogen absorption is observed the palladium catalyst is filtered off and the filtrate is added to 750 ml of chlorobenzene. The water is expelled from this mixture by azeotropic distillation to give 1150 g of a suspension containing 2-(2-chloroethoxy)-benzenesulfonic acid sodium salt.

(c) 1150 g of the above obtained chlorobenzenous suspension is diluted with 600 ml of chlorobenzene and heated to +90° C. After addition of 6.8 g dimethylformamide 120 g (1.2 moles) of phosgene is bubbled through the mixture. The reaction mixture is kept at +90° C. during 2–3 hours and then is quenched with 1200 ml water at a temperature of +70° C. The lower organic layer is separated at +60° C. to +65° C. and reacted with 160 g of a 30% aqueous ammonia solution. When all of the ammonia is added, the resulting suspension is kept at +60° C. for one hour and then filtered at +100° C. over charcoal to remove inorganic salts. The water in the filtrate is removed by azeotropic distillation. Crystallisation of the product is induced by cooling the chlorobenzene solution to +10° C. The colourless cristalline precipitate is filtered off and dried under vacuum affording 170 g (70% of theory) of 2-(2-chloroethoxy)-benzenesulfonamide having a melting point of 117°–118° C.

EXAMPLE P4

2-(2-Chloroethoxy)-benzenesulfonamide

In a process according to Example P3 the first reaction step (a) may be replaced by the following procedure: 123.8 g of chlorosulfonic acid are added over 2 hours to a suspension of 203 g of 4-chloro-(2-chloroethoxy)-benzene in 380 g of n-decane at a temperature in the range from −10° C. to +5° C. Hydrogen chloride gas is evolved. The final suspension is kept for another two hours at −10° C. to +5° C. After that the reaction mixture is quenched with 400 ml of water and extracted with 300 ml xylene at 20°–40° C. The aqueous layer was then separated and neutralized with 158 g of a 30% aqueous solution of sodium hydroxide at a temperature in the range from +60° C. to +65° C. The aqueous layer (885 g) is separated hot and directly used for the hydrogenation.

Reaction steps (b) and (c) are performed as described in Example P3.

What is claimed is:

1. A process for the preparation of 2-(2-chloroethoxy)-benzenesulfonamide of formula I

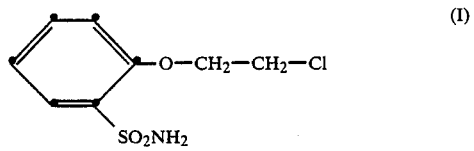

which process comprises the etherification of 4-chlorophenol of formula II

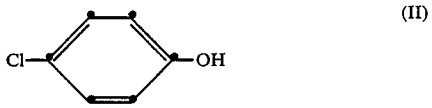

with ethylene carbonate at a temperature between +130° C. and +150° C. and chlorination of the resulting 4-(2-hydroxyethoxy)-chlorobenzene of formula III

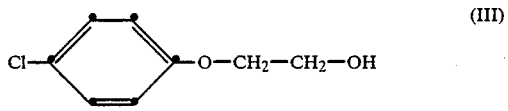

with phosgene or thionyl chloride at a temperature between +70° C. and +90° C. to give 4-(2-chloroethoxy)-chlorobenzene of formula IV

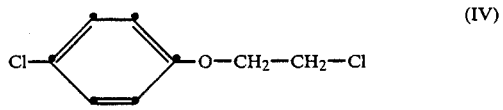

which is converted with chlorosulfonic acid, at a temperature between −20° C. and +60° C. and subsequent neutralizaion with sodium hydroxide to the sulfonic acid sodium salt of formula V

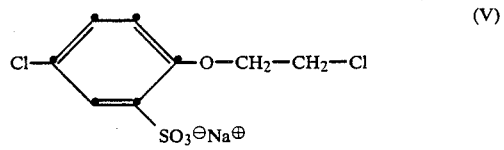

which is hydrogenated at a temperature between +20° C. and +70° C. to the compound of formula VI

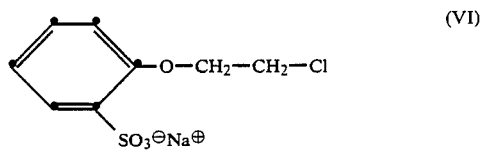

which is subsequently reacted with phosgene at a temperature between +60° C. and +120° C. to the sulfonic acid chloride of formula VII

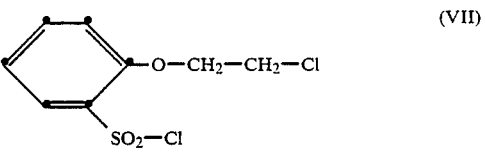

which is reacted with ammonia at a temperature between 0° C. and +100° C. to the sulfonamide of formula I.

2. A process according to claim 1, wherein the reaction of the compound of formula II to result in the compound of formula IV is carried out, without isolating the intermediate of formula III, by reacting the compound of formula II first with ethylene carbonate and subsequently treating the resulting reaction mixture with phosgene or thionyl chloride.

3. A process according to claim 2, wherein the compound of formula II is reacted with ethylene carbonate in the presence of a catalytic amount of tributylamine at a temperature between +130° C. and +150° C., and the resulting reaction mixture is treated with phosgene or thionyl chloride in the presence of a catalytic amount of dimethylformamide at a temperature between +70° C. and +90° C.

4. A process according to claim 1, wherein the compound of formula IV is reacted to compound V, at a temperature in the range from −20° C. to +60° C., with 1 equivalent of chlorosulfonic acid in hexane or n-decane, and the solution is neutralized with aqueous sodium hydroxide, at a temperature in the range from +50° C. to +90° C.

5. A process according to claim 4, wherein the compound of formula IV is reacted to compound V, at a temperature in the range from −10° C. to +5° C., with 1 equivalent of chlorosulfonic acid in hexane or n-decane, and the solution is quenched with water and extracted with xylene or toluene, neutralized with aqueous sodium hydroxide, at a temperature in the range from +50° C. to +70° C.

6. A process according to claim 1, wherein the dechlorination of the compound of formula V to result in the compound of formula VI is carried out with hydrogen, in the pressure range from 1 to 5 bar, at a temperature in the range from +20° C. to +70° C. and in the presence of a 5% palladium on carbon catalyst in a mixture of base and water.

7. A process according to claim 1, wherein the sulfonic acid chloride of formula VII is reacted with an aqueous solution of ammonia in the presence of chlorobenzene to yield the compound of formula I.

8. A process according to claim 1, wherein the reaction of the compound of formula IV to the compound of formula I, is carried out without isolating the intermediates of formulae V, VI and VII.

9. A process according to claim 1, wherein the reaction of the compound of formula II to the compound of formula I is carried out without isolating the intermediates of formulae III, V, VI and VII.

10. A process according to claim 8, wherein the compound of formula IV is treated with 1 equivalent of chlorosulfonic acid or with a slight excess thereof in cyclohexane or n-decane at a temperature between +20° C. and +60° C.; neutralized with aqueous sodium hydroxide at a temperature between +50° C. and +90° C.; dechlorinated with hydrogen in the presence of an acid acceptor, in the pressure range from 1 to 5 bar at a temperature between +20° C. and +70° C. and in the presence of a 5% palladium on carbon catalyst; converted to the sulfonic acid chloride by treatment of the mixture with phosgene at a temperature between +60° C. and +120° C.; and subsequently reacted to the final product by treatment of the reaction mixture with an aqueous solution of ammonia.

11. A process according to claim 10, wherein the compound of formula IV is treated with 1 equivalent of chlorosulfonic acid in hexane or n-decane at a temperature between −10° C. and +5° C.; quenched with water and extracted with xylene neutralized with aqueous sodium hydroxide at a temperature between +50° C. and +70° C.; dechlorinated with hydrogen in the presence of an acid acceptor, in the pressure range from 1 to 5 bar at a temperature between +20° C. and +70° C. and in the presence of a 5% palladium on carbon catalyst; converted to the sulfonic acid chloride by treatment of the mixture with phosgene at a temperature between +60° C. and +120° C.; and subsequently reacted to the final product by treatment of the reaction mixture with an aqueous solution of ammonia.

12. A process according to claim 1, wherein the compound of formula II is reacted with ethylene carbonate in the presence of a catalytic amount of tributylamine at a temperature between +130° C. and +150° C.; the resulting reaction mixture is treated with phosgene or thionyl chloride in the presence of a catalytic amount of dimethylformamide at a temperature between +70° C. and +90° C. yielding the compound of formula IV, which after purification is treated with 1 equivalent of chlorosulfonic acid in hexane or n-decane at a temperature between −10° C. and +5° C.; neutralized with aqueous sodium hydroxide at a temperature between +50° C. and +90° C.; dechlorinated with hydrogen in the pressence of an acid acceptor, in the pressure range form 1 to 5 bar at a temperature between +20° C. and +70° C. and in the presence of a 5% palladium on carbon catalyst; converted to the sulfonic acid chloride by treatment of the mixture with phosgene at a temperature between +60° C. and +120° C.; and subsequently reacted to the final product by treatment of the reaction mixture with an aqueous solution of ammonia.

13. A process according to claim 12, wherein the compound of formula II is reacted with ethylene carbonate in the presence of a catalytic amount of tributylamine at a temperature between +130° C. and +150° C.; the resulting reaction mixture is treated with phosgene or thionyl chloride in the presence of a catalytic amount of dimethylformamide at a temperature between +70° C. and +90° C. yielding the compound of formula IV, which after purification is treated with 1 equivalent of chlorosulfonic acid in n-decane at a temperature between −10° C. and +5° C.; quenched with water and extracted with xylene, neutralized with aqueous sodium hydroxide at a temperature between +50° C. and +70° C.; dechlorinated with hydrogen in the presence of sodium hydroxide, in the pressure range from 1 to 4 bar at a temperature between +40° C. and +60° C. and in the presence of a 5% palladium on carbon catalyst; converted to the sulfonic acid chloride by treatment of the mixture with phosgene at a temperature of +95° C.; and subsequently reacted to the final product by treatment of the reaction mixture with an aqueous solution of ammonia at a temperature of +60° C.

* * * * *